United States Patent
Smith et al.

(10) Patent No.: US 6,281,162 B1
(45) Date of Patent: Aug. 28, 2001

(54) ISOMERIZATION OF OLEFINS

(75) Inventors: Robert Scott Smith, Houston; Jos Peter Wristers, Clear Lake Shores, both of TX (US)

(73) Assignee: Exxon Mobil Chemical Patents Inc, Houston, TX (US)

( * ) Notice: Subject to any disclaimer, the term of this patent is extended or adjusted under 35 U.S.C. 154(b) by 0 days.

(21) Appl. No.: 09/501,652

(22) Filed: Feb. 10, 2000

Related U.S. Application Data

(62) Division of application No. 09/163,071, filed on Sep. 29, 1998, now Pat. No. 6,075,175.

(51) Int. Cl.[7] ............................... B01J 23/02; B01J 23/70
(52) U.S. Cl. .......................... 502/344; 502/346; 502/355
(58) Field of Search .................................. 502/344, 355, 502/346

(56) References Cited

U.S. PATENT DOCUMENTS

| | | | | |
|---|---|---|---|---|
| 4,810,688 | * | 3/1989 | Ewert et al. | 502/174 |
| 5,126,306 | * | 6/1992 | Drake et al. | 502/174 |
| 5,292,985 | * | 3/1994 | Lattner et al. | 585/671 |
| 5,589,602 | * | 12/1996 | Smith et al. | 585/671 |
| 5,981,820 | * | 11/1999 | Smith et al. | 585/671 |

* cited by examiner

Primary Examiner—Elizabeth D. Wood

(57) ABSTRACT

A process for catalytically isomerizing olefins, particularly for isomerizing alkenyl bridged ring compounds to the corresponding alkylidene bridged ring compounds. The catalyst is prepared by forming a dispersion of a metallic alkali metal on a support with simultaneous exposure to oxygen.

19 Claims, No Drawings

ISOMERIZATION OF OLEFINS

CROSS-REFERENCE TO RELATED APPLICATION

This application is a divisional of U.S. patent application Ser. No. 09/163,071 filed Sep. 29, 1998, now U.S. Pat. No. 6,075,175.

FIELD OF THE INVENTION

The present invention relates to a process for catalytically isomerizing olefins, particularly for isomerizing alkenyl bridged ring compounds to the corresponding alkylidene bridged ring compound.

BACKGROUND OF THE INVENTION

Olefins often are isomerized to produce different olefins, having different double bond positions, different structures, or both, as maybe necessary for a chemical synthesis or for a process for making fuels or fuel additives. For instance, 5-ethylidene-2-norbornene ("ENB") is used as a monomer in the production of rubbery polymers. ENB is produced most conveniently by catalytically isomerizing 5-vinyl-2-norbornene ("VNB"). VNB is produced by reacting 1,3-butadiene (BD) with cyclopentadiene (CPD) in an addition reaction commonly known as a Diels-Alder reaction.

Olefin isomerization catalysts include liquid bases, such as mixtures of alkali metal hydroxides and aprotic organic solvents, mixtures of alkali metal amides and amines, and mixtures of organic alkali metal compounds and aliphatic amines. Unfortunately, the catalytic activities of the liquid bases are relatively low, and therefore large amounts of these relatively expensive catalysts must be used. In addition, recovery of the catalyst from the olefin isomerization reaction mixture is very difficult—requiring complicated separation and recovery steps, producing a substantial amount of waste that must be disposed of, and consuming a large amount of energy.

Examples of solid olefin isomerization catalysts are alkali metals supported on high surface area anhydrous supports such as activated carbon, silica gel, alumina and the like. These solid catalysts are difficult to handle because they may ignite and lose activity on contact with oxygen. Also, the isomerization performance of these catalysts is generally poor—both conversion of the feed and selectivity to the desired product are low.

Solid catalysts tend to be either pyrophoric or lacking in desirably high activity. Many of the more active solid catalysts must be separately activated or stabilized in the presence of an oxygen containing gas after the catalyst is synthesized. Isomerization catalysts are needed which do not require separate activation and which also are more resistant to reactive poisons in the olefin feed.

SUMMARY OF THE INVENTION

The present invention provides a process for catalytically isomerizing a stream comprising an olefin feedstock, said process comprising: contacting said stream with a catalyst under first conditions effective to isomerize said olefin feedstock to produce a product, wherein said catalyst is prepared by a method comprising: providing a dried support; thermally mixing a metallic alkali metal with said dried support under second conditions effective to produce a mixture comprising a dispersion of said alkali metal on said dried support, wherein said alkali metal has a given melting point and said second conditions comprise a temperature higher than said given melting point and substantially simultaneous exposure to a gas comprising in the range of from about 0.001 vol % to about 10 vol % of oxygen and a remainder of inert gases to provide a cumulative total amount of said oxygen in said gas at a molar ratio to said metallic alkali metal in the range of from about 0.05-to-1.0 (0.05/1.0) to about 1.0-to-1.0 (1.0/1.0); and recovering said product.

DETAILED DESCRIPTION OF THE INVENTION

The present invention provides a new method of making selective and efficient catalysts for a process of catalytic isomerization of olefins. The catalyst of the present invention does not require a separate activation step with an oxygen containing gas to achieve a high activity. In addition, the catalyst is more resistant to poisons that are present in the olefin feedstock. The catalyst of the present invention is prepared by thermally mixing a substantially dried support with an alkali metal at a temperature higher than the melting point of the selected alkali metal to achieve substantially uniform dispersion of the alkali metal on the dried support, and substantially simultaneously exposing the dried support and the alkali metal being thermally mixed to a gas mixture comprising oxygen or other active oxygen containing compounds. Various aspects of the process are discussed separately below.

A. Catalyst Preparation

The catalyst comprises a metallic alkali metal and a dried support material. An "alkali metal" suitable for preparation of the isomerization catalyst is selected from the group consisting of lithium, sodium, potassium, rubidium, cesium, and mixtures or alloys thereof Alloys containing elements other than Group IA of the Periodic Table of the Elements also may be used, but additional steps may be required to remove the other elements chemically or physically before the catalysts can be used for isomerizing olefins. Preferably, an alkali metal useful for preparing the catalyst of the present invention consists essentially of the metal in its elemental (metallic) state. For example, if sodium is the desired metal, substantially pure metallic sodium should be used. A sodium source having a substantial amount of sodium hydroxide (about $\geq 15$ wt %) would not be suitable. Sodium, potassium, and mixtures thereof are examples of preferred alkali metals. A more preferred alkali metal consists essentially of metallic sodium. While all of the pure alkali metals are solids at room temperature (about 25° C.), some of the intermetallic alloys made of pure alkali metals are liquids at ambient conditions. These alloys or mixtures may be used for preparing the catalysts of the present invention at or below room temperature (about 25° C.).

A number of materials may be used as the support. The terms "support material" and "support" are used interchangeably herein. Some of the preferred characteristics of a support include, but-are not necessarily limited to: a high surface area; inertness to the alkali metal selected; amenability to being dried to a substantially dried state or form; and sufficient physical strength and chemical integrity under catalyst preparation conditions to remain intact and, under olefin isomerization conditions, to remain active and selective. For example, oxides and/or hydroxides of metals of Groups 1A, 2A, 3A, 4A, and 4B of the Periodic Table of the Elements may be used as a support material.

Specific examples of a suitable support material for making the isomerization catalyst of the present invention include, but are not necessarily limited to, carbon, graphite, talc, clays, diatomaceous earths, magnesium oxide, calcium oxide, strontium oxide, barium oxide, aluminum oxide, gallium oxide, silicon oxide, silicoalumino oxide, titanium oxide, zirconium oxide, hafnium oxide, Celite, and rare earth oxides such as yttrium oxide and lanthanum oxide. In addition, molecular sieves such as zeolites also may be suitable supports for the present invention. While crystalline forms of many such materials are generally stable, amorphous forms also may be used. Amorphous silica-aluminas are examples of such amorphous solids which, like their crystalline counterparts, may be used as supports.

Many compounds may have more than one crystalline form or structure. These various crystalline forms, structures, or their mixtures may be used, provided that they possess the desired physical and chemical properties. For instance, if titanium oxide (also called titania) is the support of choice, then anatase, rutile, or mixtures thereof may be used. Similarly, aluminum oxide may take a variety of crystal structures—alpha, gamma, eta, theta, etc. Pure alpha alumina is not a suitable support material because its surface area generally is too low to produce a catalyst with a desirably high activity.

In general, the support should have a surface area of least about 50 $m^2/g$, preferably, at least about 100 $m^2/g$, more preferably, at least about 140 $m^2/g$. Aluminas with surface areas greater than about 140 $m^2/g$ are most preferred supports. Structurally, the aluminas may be amorphous, gamma, eta, theta, or mixtures thereof. A preferred alumina is prepared from calcining a pseudoboehmite alumina precursor having a surface area of about 240 $m^2/g$ or higher at 600° C.

A suitable support should be in a "substantially dried" or "dried" state or form before it is mixed with the metallic alkali metal. The terms "substantially dried" and "dried" are used interchangeably herein and mean that substantially all absorbed, adsorbed, and readily produced/generated water in or from the support under catalyst preparation conditions has been removed during the drying process. Depending on the starting materials and drying conditions, there may be both chemical and/or physical transformations, in addition to water removal. For instance, a starting material pseudoboehmite may be converted under the drying conditions to a dried gamma alumina. A gamma alumina obtained from aluminum sources other than pseudoboehmite also may be dried under a different set of conditions to produce the same or a different dried gamma alumina support.

Different starting materials or supports may require different ways and/or different conditions to achieve the substantially dried or dried state or form. Many methods may be used to achieve this purpose. Preferably, the support is subjected to an elevated temperature in a substantially water-free atmosphere or under vacuum. The drying is conducted at atmospheric pressure or higher, with reduced pressure (partial vacuum) being preferred. Drying typically is effected by heating the support material (a) at a temperature in the range of from about 100° C. to about 1000° C., preferably in the range from about 120° C. to about 800° C., and more preferably in the range of from about 200° C. to about 400° C., and (b) a period in the range of from about 0.05 to about 200 hours, preferably in the range of from about 0.1 to about 100 hours, more preferably in the range of from about 1 to about 20 hours. A drying temperature lower than 100° C. may be used, particularly under partial vacuum. At a lower drying temperature, a longer drying time may be needed to achieve a desirable dried state.

While many gases, including air or oxygen-containing gases, may be used in the atmosphere during drying, it is preferable, more convenient, and more cost effective to use gases to which the alkali metal used is inert or with which the alkali metal does not react significantly. The gas should be dry and preferably oil and $CO_2$ free. Preferably, an inert gas is purged through the drying vessel to sweep away any water or oxygen molecules which may be driven off from the support material by heat. Such inert gases include, but are not necessarily limited to, nitrogen, argon, helium and mixtures thereof Light alkanes such as methane, ethane, and propane also can be used as the atmosphere for drying the support, but light alkanes must be purged out of the system before the alkali metal is thermally mixed with the support material in the presence of an oxygen containing atmosphere.

The drying process also is conducted under conditions which do not substantially or significantly alter the desired physical and chemical characteristics of the support material. For instance, drying at a temperature below about 400° C. for less than about 20 hours will not significantly change the surface area of an alumina prepared from a pseudoboehmite precursor. However, drying the same alumina at a temperature above about 500° C. may result in a substantial and adverse decrease in surface area after about 20 hours. Prolonged drying of crystalline supports at very high temperature also may destroy the crystallinity and change the support into an amorphous form.

After drying, the support material preferably is kept under a dry and inert atmosphere so that moisture (water) or any other compounds that can react with the alkali metal will not react with, be re-adsorbed by, or otherwise be associated with the dried support material. Nitrogen is a preferred inert gas for this purpose. A vacuum environment also is suitable for most supports to maintain the dried state.

In order to prepare a suitable catalyst, a substantially dried support as described above is provided and thermally mixed with from about 1 wt % to about 40 wt % of an alkali metal (on the basis of the weight of the dried support). The mixing occurs at an elevated temperature and substantially simultaneously the mixture is exposed to a gas comprising in the range of from about 0.001 vol % to about 10 vol % of oxygen or other active oxygen containing compounds, with the remainder of the gas mixture comprising an inert gas or gases. Other active oxygen containing compounds include, but are not necessarily limited to singlet oxygen, ozone ($O_3$), $N_2O$, NO, and mixtures thereof. Oxygen is a preferred gas.

An elevated temperature means a temperature higher than the melting point or the highest melting point, if there is more than a single melting point, of the alkali metal, the alkali metal alloy, or the alkali metal mixture selected for a particular catalyst. During the catalyst preparation procedure, the elevated temperature should be sufficiently high to provide a fully melted and reasonably free flowing alkali metal to ensure a uniform or substantially uniform dispersion of the alkali metal on the support. The combination of an elevated temperature and mixing is herein referred to as thermal mixing.

The contact between an alkali metal and a support material during thermal mixing may be carried out in a fixed bed, a fluidized bed, a moving bed, a stirred tank, a continuously stirred tank, or any other suitable reactor configuration. The mixing or agitation may be provided or achieved by mechanically or magnetically driven stirring and agitation or the motion and movement created in a fluidized bed. Other types of blending, mixing and agitation methods known in the art may be used as well.

The thermal mixing of the alkali metal with the support material and the simultaneous exposure to an active oxygen containing gas mixture may be achieved by having the gas mixture flowing through the catalyst preparation vessel. In this flowing mode, the gas mixture may flow at a rate in the range of from about 3 linear ft/hr to about 100 linear ft/hr. The flowing gas mixture also may serve as a lifting gas in a fluidized bed system. The flow rates are measured at ambient conditions—about 25° C. and one atmosphere pressure. Alternately, a static mode may be used. Other known methods of achieving contact between a gas and a solid also may be used.

The amount of oxygen or other oxygen-containing compounds in the gas mixture is in the range of from about 0.001 vol % to about 10 vol %, preferably in the range of from about 0.05 vol % to about 7 vol %. The remainder of the gas mixture comprises an inert gas such as nitrogen, helium, argon, and mixtures thereof.

The amount of oxygen suitable or needed for preparing an active catalyst is measured by the molar ratio ($O_2/Na$) of (a) total oxygen flowing through the catalyst preparation vessel or exposed to the catalyst to (b) the alkali metal present on the catalyst support. A suitable molar ratio of total oxygen to alkali metal is in the range of from about 0.005-to-1.0 (0.005/1.0) to about 2.0-to-1.0 (2.0/1.0). A preferred molar ratio of total oxygen to alkali metal is in the range of from about 0.05-to-1.0 (0.05/1.0) to about 1.0-to-1.0 (1.0/1.0), more preferably in the range of from about 0.1-to-1.0 (0.1/1.0) to about 0.5-to-1.0 (0.5/1.0). While a catalyst of good performance still may be obtained if too much oxygen or other active oxygen containing compounds are present, the preparation will not result in a catalyst with optimum performance. Similarly, if too little or no oxygen is used, optimum catalyst performance will not be obtained.

B. Isomerization of Olefins

The catalysts described above are used to isomerize olefins according to the following general procedure.

As used herein, the term "isomerization of olefins" relates to the movement of an olefinic double bond from an initial position to a different position in the olefinic feedstock molecule. The catalyst described herein may be used to isomerize any olefin with three or more carbon atoms. For instance, linear alpha olefins, such as 1-butene, 1-pentene, 1-hexene, 1-heptene, and 1-octene, may be isomerized to yield internal olefins, including thermodynamically and kinetically accessible cis-, trans-, E-, and Z- isomers, such as 2-butene, 2-pentene, 2-hexene, 3-hexene, 2-heptene, 3-heptene, 2-octene, 3-octene, and 4-octene. Additionally, branched alpha olefins, such as 2-methyl-1-butene and 3-methyl-1-pentene, may be isomerized to the corresponding internal olefins, 2-methyl-2-butene and 3-methyl-2-butene, respectively. Internal olefins and branched internal olefins also may be isomerized to any other thermodynamically and/or kinetically accessible isomers according to the invention.

The catalyst of the present invention can be used to isomerize alkenyl bridged ring compounds, such as VNB, to alkylidene bridged ring compounds, such as ENB. Alkenyl bridged compounds have the general formula (I):

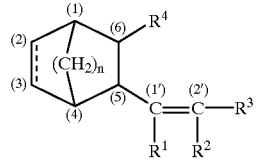

[I]

wherein $R^1$, $R^2$, and $R^3$ are each hydrogen or an alkyl group having 1 to 8 carbon atoms, $R^4$ is hydrogen or an alkyl group having 1 to 4 carbon atoms, and n is 1 or 2 and wherein a double bond may be present at the place between the 2- and 3- positions as indicated by the dotted line.

Specific examples of suitable alkenyl bridged ring compounds include, but are not necessarily limited to: 5-vinylbicyclo[2,2,1]heptane; 5-(1'-propenyl)bicyclo[2,2,1]-heptane; 5(1'-butenyl)bicyclo[2,2,1]heptane; 5-isopropenylbicyclo[2,2,1]heptane; 5-(2'-methyl-1'-propenyl)bicyclo[2,2,1]heptane; 6-methyl-5-vinylbicyclo[2,2,1]heptane; 6-methyl-5 -isopropenylbicyclo[2,2,1]heptane; 6-ethyl-5-vinylbicyclo[2,2,1]heptane; 5-vinylbicyclo[2,2,1]hepta-2-ene; 5-(1'-propenyl)-bicyclo[2,2,1]hepta-2-ene; 5-(1'-butenyl)bicyclo[2,2,1]hepta-2-ene; 5-isopropenylbicyclo[2,2,1]hepta-2-ene; 5-(2'-methyl-1'-propenyl)bicyclo[2,2,1]hepta-2-ene; 5-(1'-octenyl)bicyclo[2,2,1 ]hepta-2-ene; 6methyl-5-vinylbicyclo[2,2,1]hepta-2-ene; 6-methyl-5-isopropenylbicyclo[2,2,1]-hepta-2-ene; 6-ethyl-5-vinylbicyclo[2,2,1]hepta-2-ene; 5-vinylbicyclo[2,2,1]octane; 5-(1'-propenyl)-bicyclo[2,2,2]octane; 5-isopropenylbicyclo[2,2,2]octane; 5-(1'-butenyl)bicyclo[2,2,2]-octane; 6-methyl-5-vinylbicyclo[2,2,2]octane; 6-methyl-5-isopropenylbicyclo[2,2,2]-octane; 5-vinylbicyclo[2,2,2]octane; 5-(1'-propenyl)bicyclo[2,2,2]octa-2-ene; 5-iso-propenylbicyclo[2,2,2]octa-2-ene; 5-(1'-butenyl)bicyclo[2,2,2]octa-2-ene; 5-(2"-methyl-1'-propenyl)bicyclo[2,2,2]octa-2-ene; 6methyl-5-vinylbicyclo[2,2,2]octa-2-ene; and 6-methyl-5-isopropenylbicyclo[2,2,2]octa-2-ene.

The compounds represented by formula I can be produced, for example, by subjecting a cyclic diene, such as cyclopentadiene, and an aliphatic 1,3-diene to a Diels-Alder reaction as described in *Dienes in the Diels-Alder Reaction* by F. Fringuelli and A. Tatticchi, Wiley Intersciences, 1990. This reference is incorporated in its entirety herein by reference.

Isomerization of an alkenyl bridged ring compound shifts the olefinic double bond from the 1'-2' position to the 5-1' position of formula I, thereby forming an alkylidene bridged ring compound. The isomerization is effected by contacting a stream of an alkenyl bridged ring compound, for example, a VNB stream, with the catalyst at an isomerization temperature in the range of from about –50° C. to about 200° C. A preferred temperature for isomerization is in the range of from about 0° C. to about 150° C., more preferably temperature is in the range of from about 10° C. to about 100° C. If the starting olefin isomerization reaction temperature is 50° C. or higher, it is preferable that the final reaction temperature be brought to lower than about 30° C. in order to achieve high equilibrium conversions. In many cases, thermodynamic equilibrium at a lower temperature favors the desired product.

The present invention is particularly useful in the production of ENB from VNB. The VNB stream to be isomerized may be 90% or more by volume of VNB, or the VNB stream may be diluted with a solvent that is inert during the isomerization process. Appropriate solvents include, but are not necessarily limited to, aliphatic compounds such as hexane, heptane, octane, and isooctane, and aromatic compounds such as benzene, toluene, xylene, and ethylbenzene.

Although a feedstock of an alkenyl bridged ring compound can be obtained in high purity by distillation, it is more convenient and economically attractive to use a feedstock of lesser purity. However, many of the impurities remaining in the feedstock can react with strong base catalysts and act as catalyst poisons. Such poisons may reduce catalyst activity, catalyst life, and/or product selectivity. The catalysts of the present invention showed surprisingly high activity and good poison resistance.

Typical reactive impurities include acidic oxygenates and certain cyclic compounds containing at least two double bonds, or at least one double bond and one triple bond. Some examples are: cyclopentadiene (CPD), dicyclopentadiene (DCPD), methylcyclopentadiene (MCPD), dimethylcyclopentadiene (DMCPD), cyclopentadiene-methylcyclopentadiene dimer, cyclooctadiene (COD), indene, tetrahydroindene (THI), vinylnorbornadiene (VNBD); ethynylnorbornene (EYNB); vinylcyclohexene (VCH); methylvinylcyclohexene (MVCH); and organic hydroperoxides.

The invention will be better understood with reference to the following examples, which illustrate, but do not limit the invention, which is solely defined by the claims.

EXAMPLE 1

A 30 g gamma alumina sample with a surface area of 167 $m^2$ g and a 1.2 wt % loss-on-ignition (LOI) at 1150° C. was dried at 400° C. for one hour under nitrogen and cooled to room temperature under nitrogen. The dried alumina and 4.5 g of metallic sodium which was cut into small pieces were placed under nitrogen in a 300 ml round-bottomed flask equipped with a mechanically driven stir paddle. The dried alumina-sodium mixture was heated in the flask by a heating mantle from room temperature to a 150° C. skin temperature under nitrogen. When the metallic sodium started to melt, stirring by the mechanically driven paddle was started. The stirring continued for 2.5 hours at the 150° C. temperature and then the mixture was cooled to room temperature (about 25° C.).

EXAMPLE 2

A 30 g gamma alumina sample with a surface area of 167 $m^2/g$ and a 1.2 wt % loss-on-ignition (LOI) at 1150° C. was dried at 400° C. for one hour under nitrogen and cooled to room temperature under nitrogen. The substantially dried alumina and 3.75 g of metallic sodium in small pieces were placed under nitrogen in a 300 ml round-bottomed flask equipped with a mechanically driven stir paddle.

The dried alumina-sodium mixture was heated by a heating mantle from room temperature to 150° C. skin temperature under nitrogen. When the metallic sodium started to melt, stirring by the mechanically driven paddle was started. The stirring continued for 2.5 hours at 150° C. and then the mixture was cooled to room temperature (about 25° C.). A 5 vol % $O_2$ in $N_2$ was introduced into and flowed through the reactor at a rate of 126 ml/min until the mole ratio of $O_2$ to Na reached 0.17 to 1.

EXAMPLE 3

A 30 g gamma alumina sample with a surface area of 167 $m^2/g$ and a 1.2 wt % loss-on-ignition (LOI) at 1150° C. was dried at 400° C. for one hour under nitrogen and cooled to room temperature under nitrogen. The substantially dried alumina and 3.75 g of metallic sodium in small pieces were placed under nitrogen in a 300 ml round-bottomed flask equipped with a mechanically driven stir paddle.

Simultaneously, a 5 vol % $O_2$ in $N_2$ was introduced into and flowed through the reactor at a rate of 6 l/hr while the mixture was heated to 150° C. and stirred by the mechanically driven paddle. The flow of the 5 vol % $O_2$ in $N_2$ mixture continued during the next 90 minutes until a total mole ratio of $O_2$ to Na reached about 0.17 to 1.

EXAMPLE 4

A 25 lb lot of the same gamma alumina as used in Example 1 was added to a cylindrical vessel. The alumina was fluidized with a 9 linear-ft/hr $N_2$ flow and stirred with a cylindrical cage style mechanically driven turbine turning at about 20–30 rpm. The alumina was heated to 400° C. for one hour and then cooled to 150° C. to produce a substantially dried support.

Separately, 3.75 pounds of sodium metal were charged to a tank which was connected to the cylindrical vessel with a valve. The sodium was melted at 150° C. under nitrogen. The molten sodium metal was stored in the tank under nitrogen and was added drop-wise through the valve in a period of one hour to the dried alumina which was fluidized with a 1 vol % $O_2$ in $N_2$ gas mixture and mechanically stirred at 150° C. After the sodium addition was completed, the mixture was maintained at 150° C. with continuing fluidization with the same $O_2$ in $N_2$ gas mixture and stirring until the mole ratio of total oxygen to sodium added reached 0.17 to 1.

EXAMPLE 5

The activities of the catalysts for olefin isomerization were tested under nitrogen by stirring the catalyst for two hours at room temperature (about 25° C.) with 5-vinyl-2-norbornene (VNB) containing small amounts of various impurities. After the two hour reaction time, the reaction mixture was analyzed by gas chromatography to determine the VNB conversion. The catalysts from Examples 1, 2, and 3 were tested with a VNB feed containing 700 ppm of vinylnorbornadiene (Column A of the Table). The amount of catalyst used in these experiments was 1.4 wt % based on the weight of VNB. The catalysts from Examples 2 and 3, both having been exposed to oxygen, were found to be more active than the catalyst from Example 1. The catalyst from Example 3, prepared according to the present invention, was more active than the catalyst from Example 2 which involved treatment with oxygen containing gas after the sodium had been deposited on the support.

The catalysts from Examples 2 and 4 were tested for their isomerization activities with a VNB feed containing 3800 ppm indene (Column B of the Table). The amount of catalyst used in these two experiments was 4.6 wt % based on the weight of VNB. The catalyst from Example 4, prepared according to the present invention, was found to be more active than the catalyst from Example 2 which involved treatment with oxygen containing gas after the sodium had been deposited on the support.

TABLE

| | | VNB Conversion (%) | |
|---|---|---|---|
| Example | Catalyst Preparation | A | B |
| 1 | Na under $N_2$ (no $O_2$) | 66 | — |
| 2 | Sequential addition of Na under $N_2$, and 5 vol % $O_2$ in $N_2$ | 96 | 34 |
| 3 | Simultaneous addition of Na and 5 vol % $O_2$ in $N_2$ | 99.1 | — |
| 4 | Simultaneous addition of Na and 1 vol % $O_2$ in $N_2$ | — | 57 |

VNB: 5-vinyl-2-norbornene
A: VNB feed contained 700 ppm vinylnorbornadiene
B: VNB feed contained 3800 ppm indene Persons of ordinary skill in the art will recognize that many modifications may be made to the present invention without departing from the spirit and scope of the present invention. The embodiments described herein are meant to be illustrative only and should not be taken as limiting the invention, which is defined in the following claims.

We claim:

1. A method for malting an olefin isomerization catalyst comprising:
   providing a dried support having a surface area of at least about 50 m²/g; and
   mixing an elemental alkali metal with said dried support under conditions effective to produce a mixture comprising a dispersion of said alkali metal on said dried support, wherein said alkali metal has a melting point and said conditions comprise a temperature higher than said melting point and said conditions further comprise simultaneous exposure of said elemental alkali metal and said dried support to a gas mixture includes from 0.001 vol % to 10 vol % of oxygen and a remainder of inert gases to provide a total amount of said oxygen in said gas mixture at a molar ratio to said elemental alkali metal from about 0.05-to-1.0 to about 1.0-to-1.0.

2. The method of claim 1 wherein said alkali metal is selected from the group consisting of lithium, sodium, potassium, rubidium, cesium, and mixtures thereof.

3. The method of claim 2 wherein said alkali metal is selected from the group consisting of sodium, potassium, and mixtures thereof.

4. The method of claim 3 wherein said alkali metal consists essentially of sodium.

5. The method of claim 4 wherein said dried support comprises alumina.

6. The method of claim 1 wherein said dried support has a surface area of at least about 140 m²/g.

7. The method of claim 1 wherein said molar ratio is from about 0.1-to-1.0 about 0.5-to-1.0.

8. The method of claim 1 wherein said exposure to a gas mixture comprises exposure in a flowing mode.

9. The method of claim 1 wherein said exposure to a gas mixture comprises exposure in a static mode.

10. The method of claim 1 wherein said dispersion is uniform.

11. A method for making an olefin isomerization catalyst comprising:
    providing a dried support having a surface area of at least about 100 m²/g; and
    mixing an elemental alkali metal with said dried support under conditions effective to produce a mixture comprising a dispersion of said alkali metal on said dried support, wherein said alkali metal has a melting point and said conditions comprise a temperature higher than said melting point and said conditions further comprise simultaneous exposure of said elemental alkali metal and said dried support to a gas mixture includes from 0.001 vol % to 10 vol % of oxygen and a remainder of inert gases to provide a total amount of said oxygen in said gas mixture at a molar ratio to said elemental alkali metal from about 0.05-to-1.0 to about 1.0-to-1.0, where said alkali metal is selected from the group consisting of lithium, sodium, potassium, rubidium, cesium, and mixtures thereof.

12. The method of claim 11 wherein said alkali metal is selected from the group consisting of sodium, potassium, and mixtures thereof.

13. The method of claim 12 wherein said metallic alkali metal consists essentially of sodium.

14. The method of claim 13 wherein said dried support comprises alumina.

15. The method of claim 11 wherein said dried support has a surface area of at least about 140 m²/g.

16. The method of claim 11 wherein said molar ratio is from about 0.1-to-1.0 to about 0.5-to-1.0.

17. The method of claim 11 wherein said exposure to a gas mixture comprises exposure in a flowing mode.

18. The method of claim 11 wherein said exposure to a gas mixture comprises exposure in a static mode.

19. The method of claim 11 wherein said dispersion is uniform.

* * * * *

UNITED STATES PATENT AND TRADEMARK OFFICE
CERTIFICATE OF CORRECTION

| | | |
|---|---|---|
| PATENT NO. | : 6,281,162 B1 | Page 1 of 1 |
| DATED | : August 28, 2001 | |
| INVENTOR(S) | : Robert Scott Smith and Jos Peter Wristers | |

It is certified that error appears in the above-identified patent and that said Letters Patent is hereby corrected as shown below:

<u>Column 9,</u>
Line 2, "malting" should be -- making --.

Signed and Sealed this

Thirty-first Day of December, 2002

JAMES E. ROGAN
*Director of the United States Patent and Trademark Office*